United States Patent

Myers et al.

(10) Patent No.: US 7,367,936 B2
(45) Date of Patent: May 6, 2008

(54) MAGNETIC STIMULATORS AND COILS THEREFOR

(75) Inventors: Anna M Myers, Newcastle upon Tyne (GB); Anthony T Barker, Sheffield (GB); David R Hose, Bamford (GB)

(73) Assignee: The Magstim Company Ltd., Whitland, Dyfed (GB)

( * ) Notice: Subject to any disclaimer, the term of this patent is extended or adjusted under 35 U.S.C. 154(b) by 724 days.

(21) Appl. No.: 10/989,872

(22) Filed: Nov. 16, 2004

(65) Prior Publication Data

US 2005/0134193 A1 Jun. 23, 2005

(30) Foreign Application Priority Data

Nov. 21, 2002 (GB) .................. 0227147.6
Nov. 20, 2003 (GB) .................. 0327025.3

(51) Int. Cl.
*A61N 2/00* (2006.01)

(52) U.S. Cl. ...................................... 600/13
(58) Field of Classification Search ............. 600/9–15; 128/897–898
See application file for complete search history.

(56) References Cited

U.S. PATENT DOCUMENTS 4,550,714 A * 11/1985 Talish et al. .................. 600/14
6,099,459 A * 8/2000 Jacobson ...................... 600/13

FOREIGN PATENT DOCUMENTS

GB 2261820 A 2/1993
GB 2264642 * 9/1993
WO 02/25675 * 3/2002

* cited by examiner

*Primary Examiner*—John P Lacyk
(74) *Attorney, Agent, or Firm*—Iandiorio Teska & Coleman

(57) ABSTRACT

A magnetic coil inductor for use in magnetic stimulators comprises two face-to-face electrically connected windings each having a multiplicity of turns of a respective conductor. Corresponding turns are separated by a gap which typically is of the order of 18 to 20% of the total height of the coil. The magnetic stimulator includes a discharge capacitor and a switch arrangement operable to provide discharge pulses at a selected repetition rate through the inductor, the inductor and the capacitor constituting a resonant circuit of which the resonant frequency is substantially in excess of the repetition rate and is typically between 2 and 6 kHz.

16 Claims, 8 Drawing Sheets

MAGNETIC STIMULATORS AND COILS THEREFOR

FIELD OF THE INVENTION

The present invention relates to magnetic stimulators, primarily intended for the magnetic stimulation of neuro-muscular tissue. The invention more particularly relates to an improved coil for use in such magnetic stimulation and stimulators including such coils.

GENERAL BACKGROUND

Known magnetic stimulators comprise generally a charging circuit, a capacitor, a large magnetic coil and a control for allowing discharge of the capacitor through the coil. The 'stimulating' coil is usually of a size adapted to fit partly over a human cranium.

The discharge capacitor may be discharged, normally by means of a switch in series between the capacitor and the coil or, in more sophisticated embodiments, by electronic switches such as thyristors which not only allow discharge of the capacitor through the coil but also facilitate the recovery of electrical energy by the capacitor from the stimulating coil. One suitable arrangement for this purpose is described in U.S. Pat. No. 5,766,124 to Polson, commonly assigned herewith. Although it is possible to provide a single discharge of the capacitor through the stimulating coil, more versatile arrangements, such as that described in the aforementioned patent, allow for repeated discharges, at a repetition frequency of typically 100 Hz. The aforementioned patent describes energy recovery systems which facilitate the provision of repeated discharges from the capacitor before another charging cycle is necessary.

In any event, the discharge of the capacitor through the coil produces for the coil a time varying magnetic field which stimulates neuro-muscular tissue. This stimulation has well-established therapeutic effects. It has been known to construct a stimulating coil for the aforementioned purposes as a generally flat circular coil, that is to say with the turns of the coil in generally the same plane or, in some cases, progressively offset planes. Owing to the very high magnetic fields required, typically of the order of currents required, the current density of the coil being typically in excess of $10^8$ amperes per meter squared, a stimulating coil is typically composed of pre-formed rectangular solid copper strips rather than wires, there being comparatively few turns, such as between ten and twenty turns, in the coil.

The discharge circuit of a magnetic stimulator of this type is of necessity a resonant LC circuit dominated by the capacitance of the discharge capacitor and the inductance of the stimulating coil. The natural resonant frequency of such a circuit is typically substantially above the aforementioned repetition frequency and is generally in the range from 2 to 6 kHz. For a resonant circuit of which the discharge capacitor has a capacitance of, typically, 90 µF and a stimulating coil having an inductance of, typically, 22 µH, the naturally resonant frequency is 3.6 kHz.

At this comparatively high frequency, owing to the electrical phenomena known as the skin and proximity effects, there is a very significant non-uniformity in the current density through the solid body of the coil. In effect the current through the coil flows through a much-reduced area, increasing the effective resistance of the coil and dissipating more energy within the coil. Although the skin effect on a single conductor is in itself slight for frequencies in the range (for example) of 1-10 kHz, it has now been found that the proximity effect of high frequency current on adjacent turns of a coil renders the current distribution very non linear and substantially increases the dynamic or high frequency resistance of the coil.

The present invention is aimed at alleviating these disadvantages.

The present invention is based on the provision of a stimulating coil which is composed of a plurality of multiple-turn windings of uniformly solid material disposed face-to-face, i.e. in adjacent parallel planes, each turn in each winding being aligned with and separated from a neighbouring turn of an adjacent winding by a gap which is selected for optimum electrical effectiveness. By 'electrical effectiveness' is meant a ratio which relates the stimulating strength, i.e. the voltage calculated to be induced across a typical nerve membrane, to the energy dissipated in the coil during stimulation. This effectiveness will be a maximum when the dynamic resistance of the coil is at a minimum.

As will become apparent the gap's height for maximum electrical effectiveness does vary with a variety of factors, such as the number of turns, the width of the turns, the total height of the coil, the radius of the coil and resonant frequency. Nevertheless, it has been found for preferred coil parameters that maximum effectiveness is achieved with a gap of the order of 18 to 20% of the total coil height (the dimension in the direction normal to the plane of the coil and including the gap).

Further features of the invention will be apparent from the following detailed description, with reference to the drawings.

DETAILED DESCRIPTION

Figure 1:
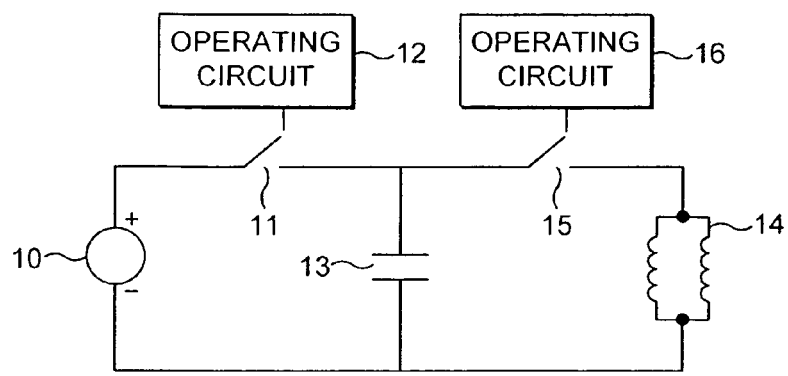
FIG. 1 is a simplified diagram of a magnetic stimulator including an improved coil according to the invention.

FIG. 1 of the drawings illustrates in a rather simplified manner one example of the electrical circuit of a magnetic stimulator according to the invention.

A direct current source 10 is connectable by way of a switch 11, under the control of an operating circuit 12, to charge a capacitor 13. This capacitor, hereinafter called the discharge capacitor, can be controllably discharged into a coil 14 by closure of a switch 15 under the control of an operating circuit 16. The resistance of the coil 14 is not shown explicitly in FIG. 1.

As will be more particularly described with reference to FIG. 2, the coil 14 comprises a plurality of similar face-to-face coil windings separated by a substantial gap. The coils may be in series or parallel though should produce additive magnetic fields.

In practice the charging circuit, namely source 10, switch 11 and capacitor 13 and the discharge circuit, namely capacitor 13, switch 15 and coil 14, are substantially more complex than is illustrated in FIG. 1. More particularly the charging circuit may comprise a storage capacitor, connected via switches to a charged transfer capacitor, likewise connected via a switch arrangement to the discharge capacitor 13 and the switch arrangement exemplified by the single switch 15 is embodied by solid state switches in both the branches between capacitor 13 and coil 14; there are also switches (operated in anti-phase with the discharging switches) to provide a current path back to the capacitor so as to recover as much energy as possible from the inductor during successive discharge pulses. A detailed circuit of this nature is the subject of the aforementioned patent to Polson herein incorporated by reference.

In any event, although a single discharge at a time is feasible, it is more usual and generally preferable to provide for a burst of discharge pulses in an operating cycle, by (in effect) repeated closure and opening of switch 15 at a repetition rate of up to 100 Hz or so.

The resonant frequency of the discharge circuit is mainly determined by the capacitance of capacitor 13 and the inductance of stimulating coil 14. Depending on the capacitance of the discharge capacitor 13, the inductance of the stimulating coil 14 may be in the range 1 µH to 1 mH. For a capacitance of approximately 90 µF for capacitor 13 and 22 µH for coil 14, the natural resonant frequency is of the order of 3.6 kHz. As mentioned previously, it is desirable that this be substantially greater, i.e at least an order of magnitude greater, than the expected repetition frequency of discharge pulses.

In order to reduce the non-uniformity of current distribution and consequent effective increase in resistance of a stimulating coil in these circumstances, the coil 14 is made as a plurality of face-to-face windings, the turns in each winding being of homogeneously solid (not being hollow), each turn of each winding each being aligned with a respective turn of the winding or windings. This is exemplified by the construction shown in FIG. 2.

Figure 2:
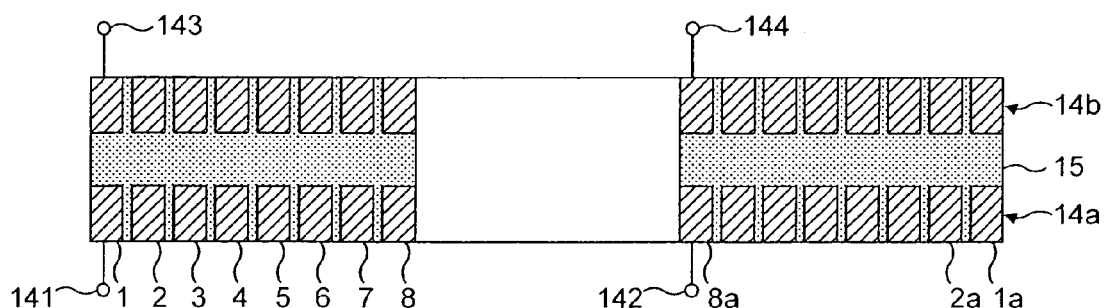
FIG. 2 is a schematic illustration, mostly in section, of an improved coil according to the invention.

In FIG. 2, there are two approximately circular coil windings 14a and 14b arranged with an intervening gap 15. Each coil is composed of a few concentric turns of a strip conductor, typically rectangular in cross-section. In FIG. 2 the successively inward turns of winding 14a are shown as 1 to 8; the other sides of corresponding turns are shown as 1a to 8a respectively. The coil has terminals illustrated schematically as 141 and 142. The coil 14b is arranged similarly, having terminals 143 and 144.

The gap 15 between the coils may be composed of a thermally conductive material but may constitute an air passage for cooling the coils by forced convection.

Figure 3:
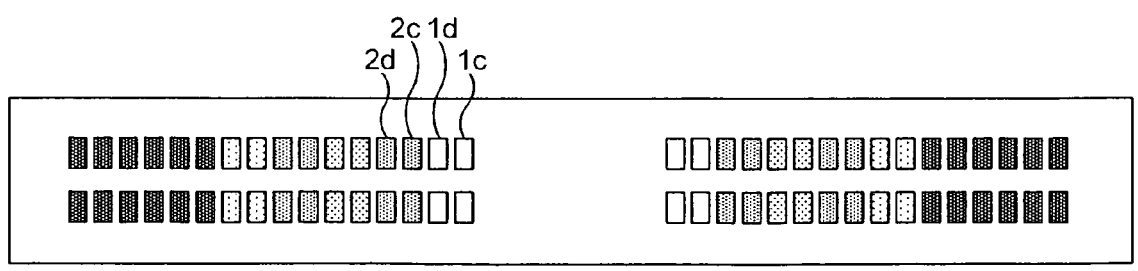
FIG. 3 illustrates a modification of the coil.

FIG. 3 illustrates a modification in which each turn of each winding is composed of two conductors which are electrically connected in parallel. Thus the inner conductor 1c of the innermost turn is connected to the inner conductor 2c in the next outer turn whereas the outer conductor of the innermost turn is connected to the outer conductor in the next outer turn and so on. This is arrangement reduces the skin and proximity effects. There may be more than two conductors making up each turn.

FIG. 3 shows the application of this interleaving of the conductors for both the adjacent windings of the coil. In both FIG. 2 and FIG. 3 each turn is aligned, in the direction normal to the planes of the windings, with a turn of the other winding.

Figure 4:
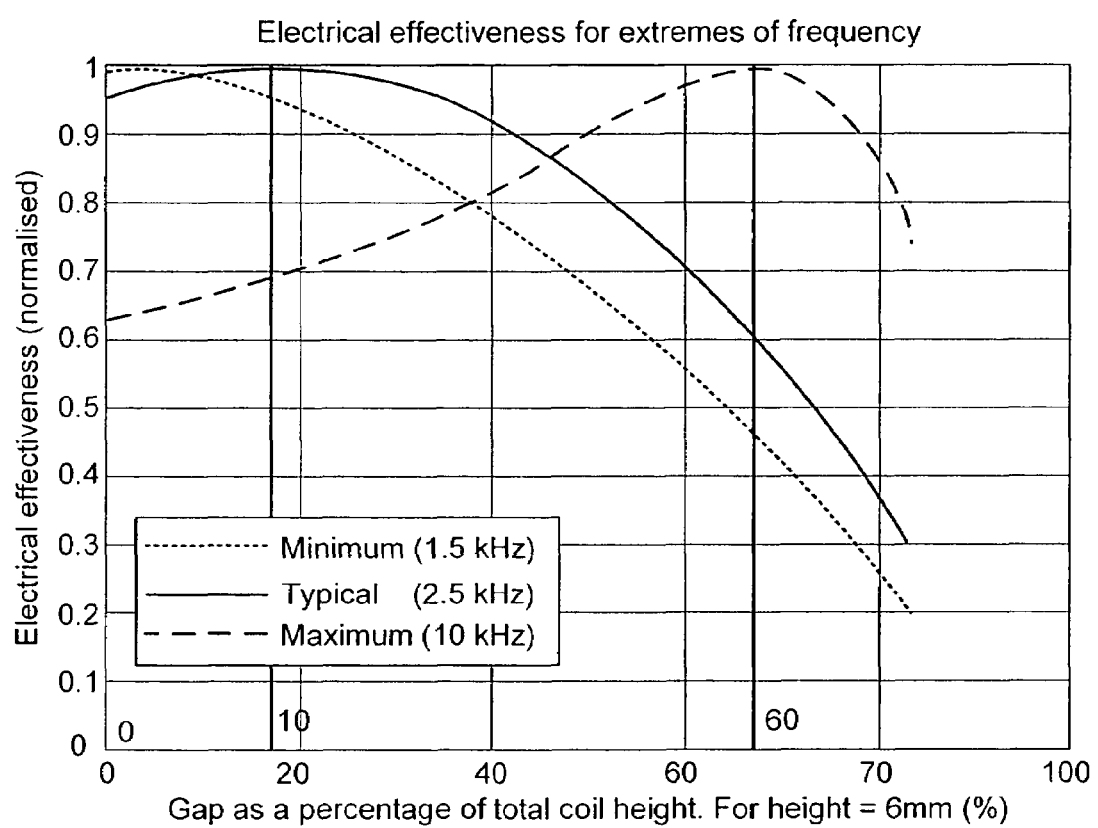
FIGS. 4 to 10 are graphs to illustrate variation of electrical effectiveness in various circumstances.

FIG. 4 is a graph illustrating the normalised electrical effectiveness of the coil against variation of the gap as a percentage of total coil height, for the specific height of 6 mm. Three graphs are shown, the dotted graph for an operating frequency of 1.5 kHz, the solid line for an operating frequency of 2.5 kHz and the dashed line for an operating frequency at 10 kHz. For the operating frequency of 2.5 kHz maximum effectiveness occurs when the gap is at 18% of the total coil height. The size of the gap at which the maximum effectiveness occurs increases with operating frequency and is at 68% of the total coil height for the maximum operating frequency of 10 kHz.

Figure 5:
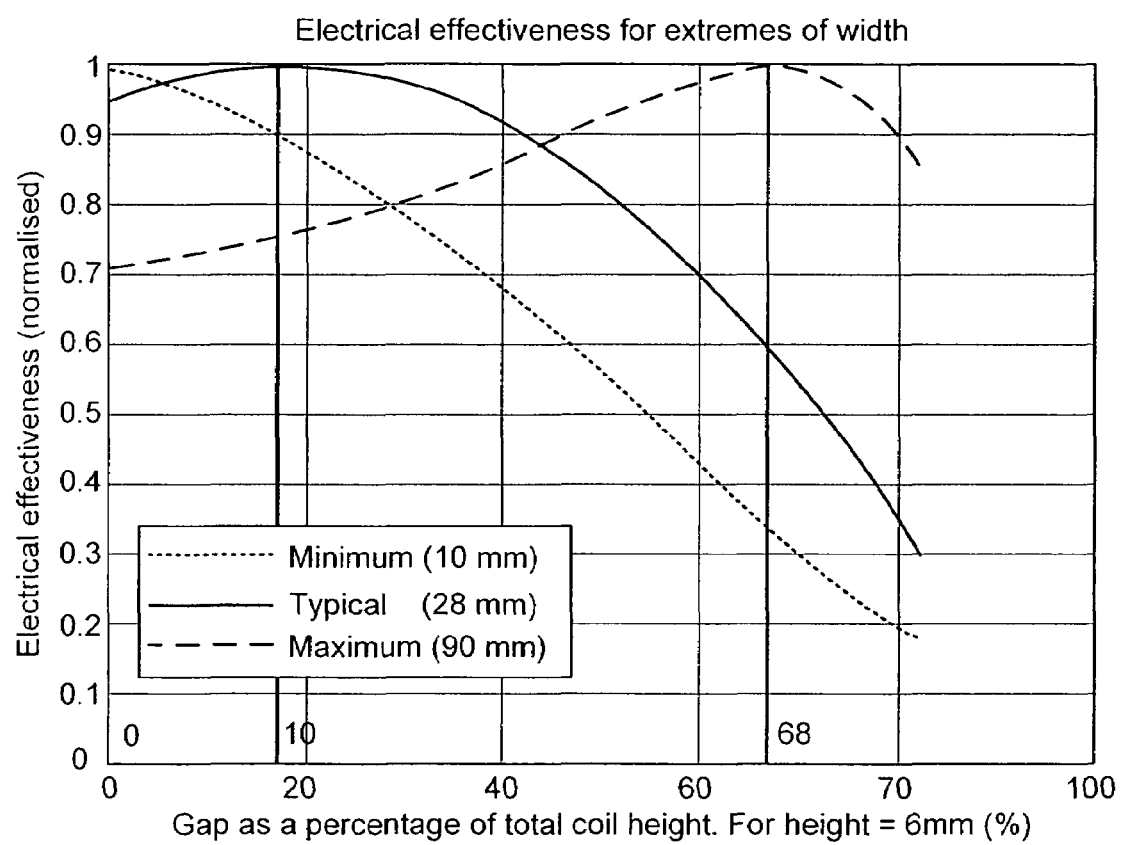

FIG. 5 shows the normalised electrical effectiveness against the gap as a percentage of coil height for a 6 mm coil height. The dotted line is for a coil width of 10 mm (coil width being the difference between the outside radius and the inside radius of the coil). The solid line is for a typical coil width of 28 mm and the dashed line for a maximum coil width of 90 mm. Again, the maximum effectiveness is provided for a gap which is 18% of the total coil height for a coil width of 28 mm. The optimum gap increases with the width of the coil and is at 68% of the total coil height for a coil of 90 mm.

Figure 6:
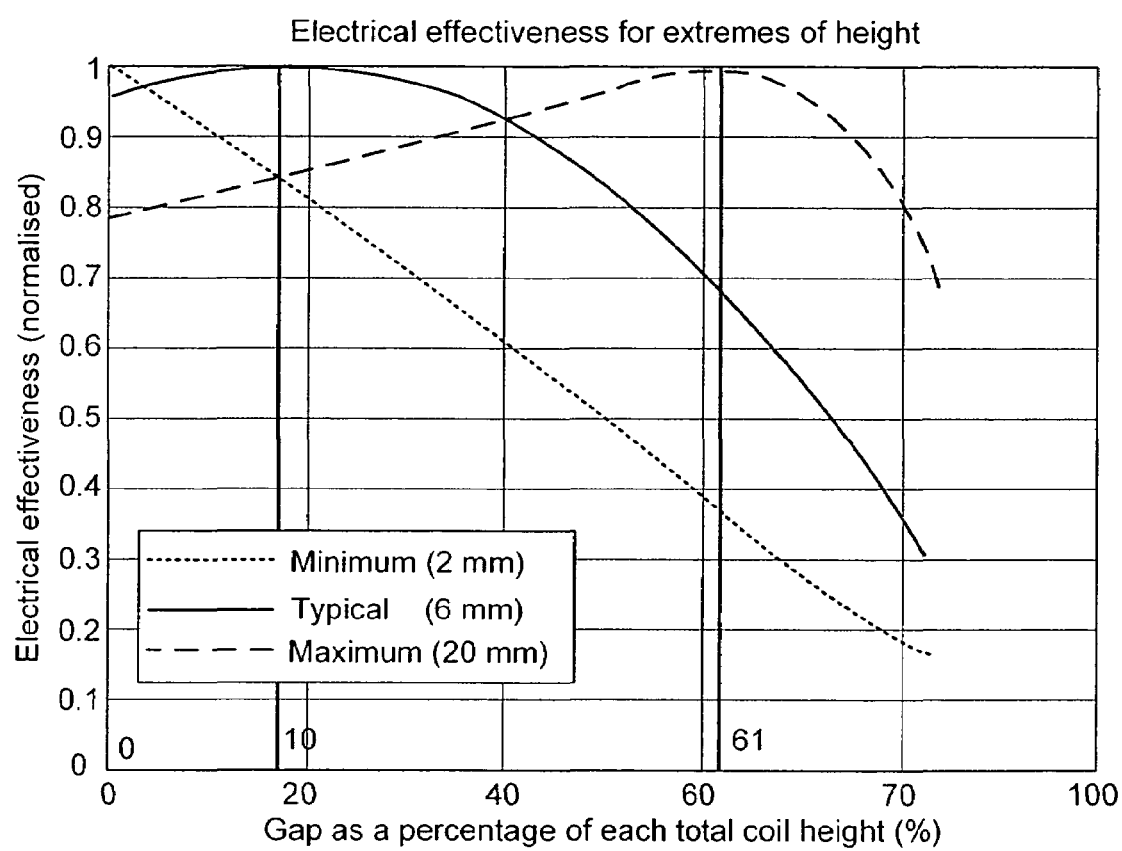

FIG. 6 shows the normalised electrical effectiveness against the gap as a percentage of total coil height. For a coil height of 6 mm, the dotted line, the optimum gap is 18% of the coil height. The dotted line shows the variation of effectiveness with gap for a total coil height of 2 mm and the dashed line shows the variation of electrical effectiveness with gap for a coil height of 20 mm. Again, the optimum gap is at 18% of the total coil height for a coil height of 6 mm. The optimum gap increases to 61% of the total coil height when the coil height is at 20 mm.

Figure 7:
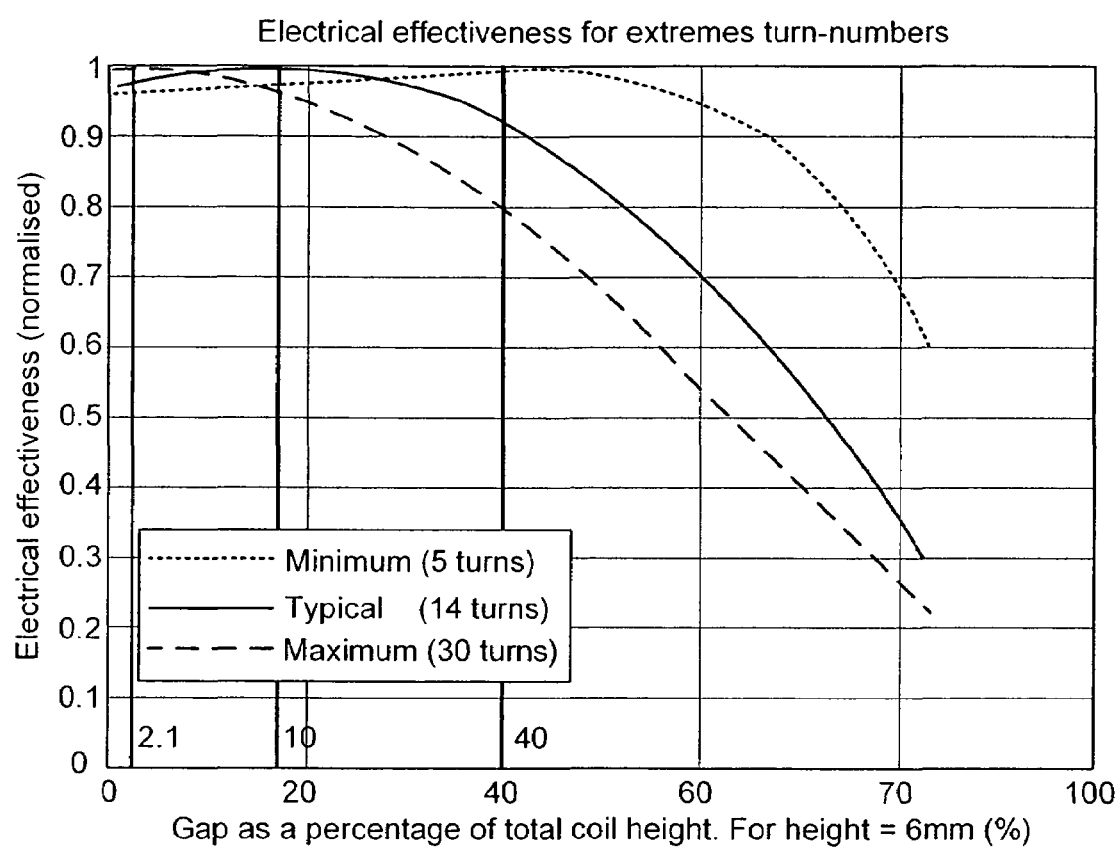

FIG. 7 illustrates the variation of normalised electrical effectiveness, with gap as a percentage of total coil height for various numbers of turns. The dotted line is for five turns, the solid line for 14 turns and the dashed lines for 30 turns. The optimum gap decreases with increase in turns, other things being equal, and for the provision of 14 turns is at 18% of the total coil height.

Figure 8:
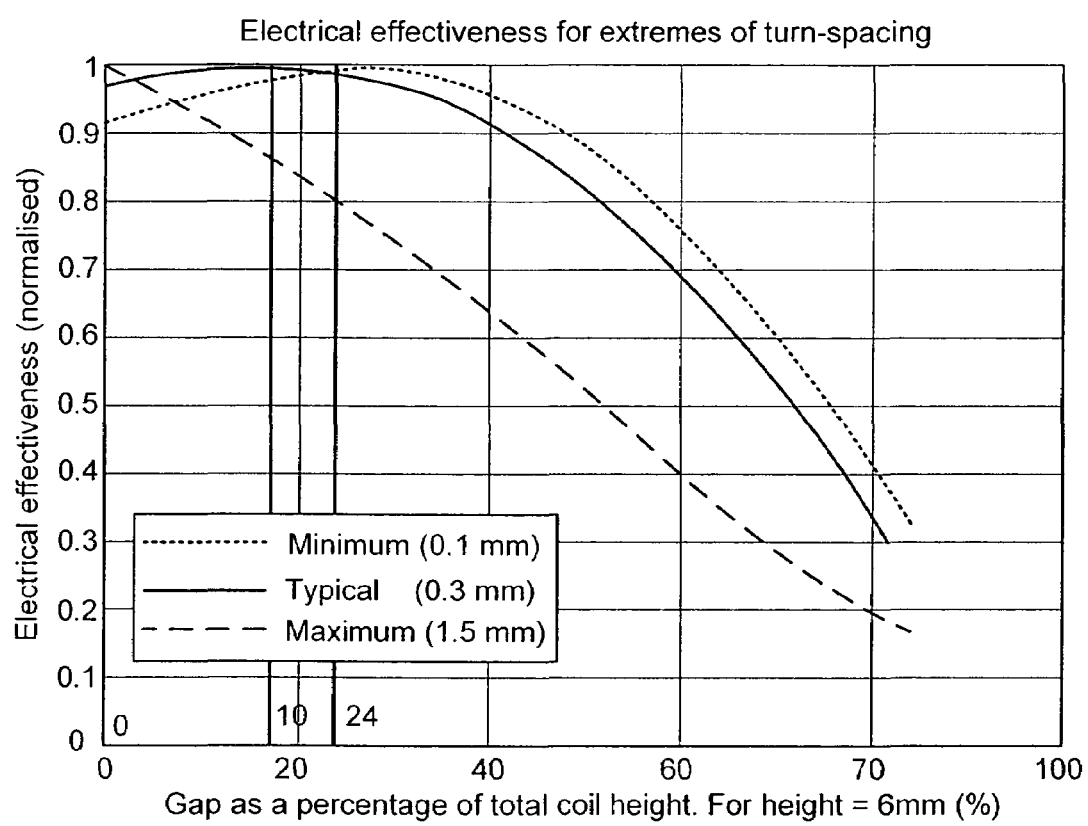

FIG. 8 illustrates the variation of electrical effectiveness with gap, as a percentage of total coil height and for a height of 6 mm, for extremes of turn spacing, the dotted line representing the variation for a 0.1 mm spacing between turns, the solid line representing the variation for a spacing of 0.3 mm between turns and the dashed line representing the variation for a 1.5 mm spacing between turns. For a 0.3 mm spacing, the optimum gap is at 18% of the total coil height whereas for a 0.1 mm spacing the optimum gap is at 24% of the total coil height.

Figure 9:
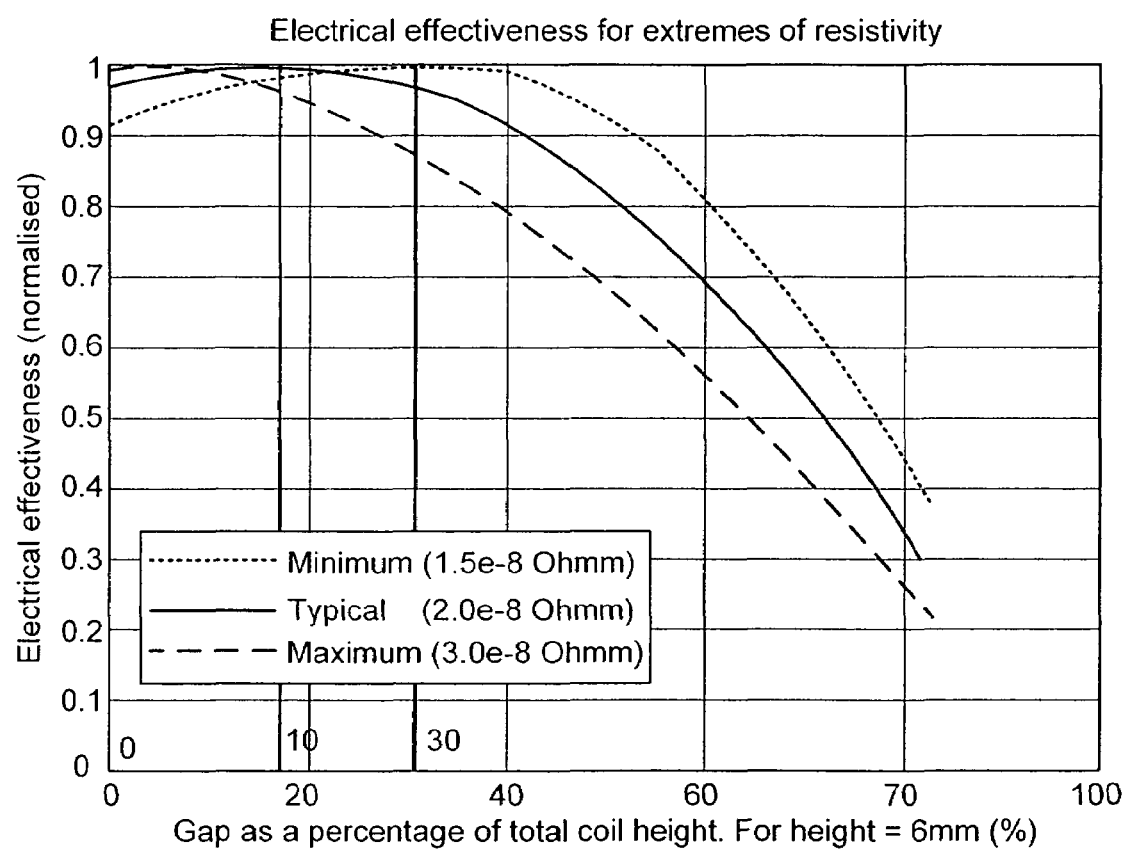

FIG. 9 illustrates variation of the electrical effectiveness with gap as a percentage of total coil height, again for a height of 6 mm, for different values of resistivity of the material. For the minimum value considered, 1.5e-8 ohmm, the optimum gap occurs at 30% of the total coil height. For a value of 2.0e-8 ohmm, the optimum gap is at 18% of the total coil height.

Figure 10:
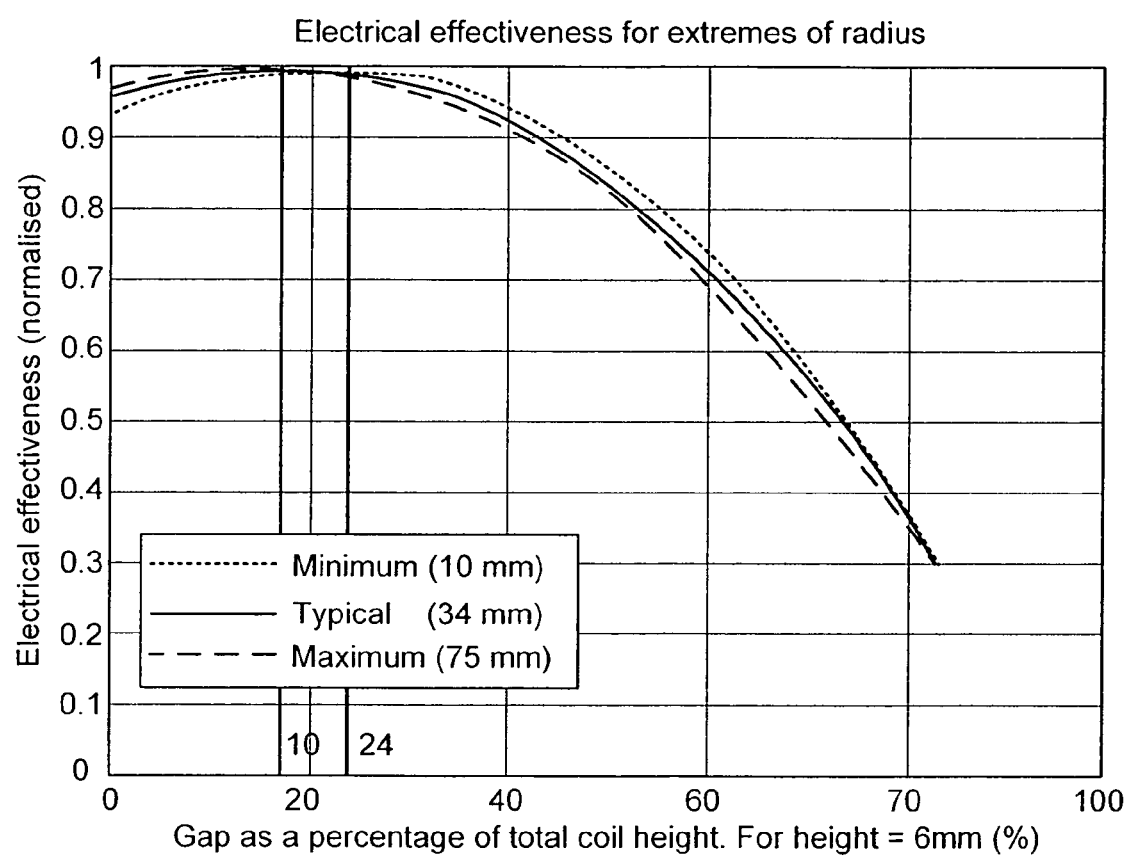

FIG. 10 illustrates the variation of electrical effectiveness with gap as a percentage of total coil height for a height of 6 mm for different values of inside radius of the coil. The dotted line is for an inside radius of 10 mm, the solid line for an inside radius of 34 mm and the dashed line for an inside radius of 75 mm. There is very little variation in the optimum gap, which is in the comparatively narrow range of 18 to 24% of the total coil height.

The foregoing graphs therefore indicate how the gap should be selected for optimum effectiveness of the coil.

We claim:

1. A magnetic coil for use in magnetic stimulators, comprising two face-to-face coil windings each having a multiplicity of turns of a respective homogeneously solid electrical conductor disposed in a respective one of two substantially parallel planes, wherein corresponding turns of said two windings are substantially aligned in a direction normal to said coil windings and are separated by a gap which is optimised for electrical effectiveness of said coil.

2. A magnetic coil as in claim 1 wherein each conductor comprises a rectangular-section conductive strip.

3. A magnetic coil as in claim 1 as in claim 1 wherein the height of said gap is substantially 18% of the total height of said coil.

4. A magnetic coil as in claim 1 wherein each coil winding has between five and thirty turns.

5. A magnetic coil as in claim 1 wherein said coil has a total coil height between 2 and 20 mm.

6. A magnetic coil as in claim 1 wherein said turns have a spacing of between 0.1 and 1.5 mm.

7. A magnetic coil as in claim 1 wherein the coil has a width between an outside radius and an inside radius between 10 and 90 mm.

8. A magnetic coil for use in magnetic stimulators, comprising two face-to-face coil windings each having a multiplicity of turns of a respective homogeneously solid electrical conductor disposed in a respective one of two substantially parallel planes; wherein:
   corresponding turns of said two windings are substantially aligned in a direction normal to said coil windings and are separated by a gap; and
   the height of said gap is of the order of 18% of the total height of said coil.

9. A magnetic coil as in claim 8 wherein each coil winding has between five and thirty turns.

10. A magnetic coil as in claim 8 wherein said coil has a total coil height between 2 and 20 mm.

11. A magnetic coil as in claim 8 wherein each coil winding has between five and thirty turns; and said turns have a relative spacing of between 0.1 and 1.5 mm.

12. A magnetic coil as in claim 8 wherein the coil has a width between an outside radius and an inside radius of between 10 and 90 mm.

13. A magnetic coil for use in magnetic stimulators, comprising two face-to-face coil windings each having a multiplicity of turns of a respective homogeneously solid electrical conductor disposed in a respective one of two substantially parallel planes, each said conductor comprising comprising a rectangular-section conductive strip capable of sustaining a current density of at least $10^8$ amperes per meter squared; and wherein corresponding turns of said two windings are substantially aligned in a direction normal to said coil windings and are separated by a gap which is optimised for electrical effectiveness of said coil.

14. A magnetic stimulator comprising:
   a discharge capacitor;
   means for charging the capacitor;
   a magnetic coil comprising:
   two face-to-face coil windings each having a multiplicity of turns of a respective homogeneously solid electrical conductor disposed in a respective one of two substantially parallel planes, wherein corresponding turns of said coil windings are substantially aligned in a direction normal to said coil windings and are separated by a gap which is optimised for electrical effectiveness of the coil; and
   a switch arrangement operable to discharge said discharge capacitor through said coil, said discharge capacitor and said coil constituting a resonant circuit of which the resonant frequency is in the range from 1.5 to 10 kHz.

15. A magnetic stimulator as in claim 14 wherein each said conductor comprising comprises a rectangular-section conductive strip capable of sustaining a current density of at least $10^8$ amperes per meter squared.

16. A magnetic stimulator as in claim 14 wherein the coil has a width between an outside radius and an inside radius between 10 and 90 mm.

\* \* \* \* \*